US009446002B2

(12) United States Patent
Chenevier et al.

(10) Patent No.: US 9,446,002 B2
(45) Date of Patent: Sep. 20, 2016

(54) SPHEROIDS AND MULTIPARTICULATE TABLETS COMPRISING THEM

(75) Inventors: Philippe Chenevier, Montreal (CA); Dominique Marechal, Laval (CA)

(73) Assignee: ETHYPHARM, Saint-Cloud Cedex (FR)

(*) Notice: Subject to any disclaimer, the term of this patent is extended or adjusted under 35 U.S.C. 154(b) by 184 days.

(21) Appl. No.: 12/766,176

(22) Filed: Apr. 23, 2010

(65) Prior Publication Data

US 2010/0203134 A1 Aug. 12, 2010

Related U.S. Application Data

(62) Division of application No. 10/530,052, filed as application No. PCT/FR03/02909 on Oct. 3, 2003, now abandoned.

(30) Foreign Application Priority Data

Oct. 4, 2002 (FR) .................................. 02 12333

(51) Int. Cl.
*A61K 9/26* (2006.01)
*A61K 9/50* (2006.01)
*A61K 9/20* (2006.01)

(52) U.S. Cl.
CPC ........... *A61K 9/5073* (2013.01); *A61K 9/2081* (2013.01); *A61K 9/5078* (2013.01)

(58) Field of Classification Search
CPC .... A61K 9/20; A61K 9/2004; A61K 9/2009; A61K 9/2013; A61K 9/2018; A61K 9/2027; A61K 9/2031; A61K 9/2095
USPC .................................................. 424/450–489
See application file for complete search history.

(56) References Cited

U.S. PATENT DOCUMENTS

| 4,832,958 A | 5/1989 | Baudier et al. |
| 4,867,985 A | 9/1989 | Heafield et al. |
| 5,780,055 A * | 7/1998 | Habib et al. .................. 424/464 |
| 5,965,163 A | 10/1999 | Miller et al. |
| 6,077,544 A | 6/2000 | Debregeas et al. |
| 6,136,344 A * | 10/2000 | Depui et al. .................. 424/470 |
| 6,221,392 B1 * | 4/2001 | Khankari et al. ............. 424/464 |
| 6,419,954 B1 * | 7/2002 | Chu et al. ..................... 424/465 |
| 6,426,087 B1 | 7/2002 | Saslawski et al. |
| 6,544,556 B1 * | 4/2003 | Chen et al. .................... 424/469 |
| 2003/0044464 A1 * | 3/2003 | Ziegler et al. ................ 424/468 |

FOREIGN PATENT DOCUMENTS

| AU | 771759 B2 | 4/2004 |
| EP | 0 195 476 A | 9/1986 |
| EP | 0 217 778 A | 4/1987 |
| EP | 1 028 718 B1 | 8/2000 |
| FR | 2 793 688 A1 | 5/1999 |
| FR | 2793688 A1 * | 11/2000 |
| WO | WO 96/01624 A | 1/1996 |
| WO | WO 99/26608 A | 6/1999 |
| WO | WO 99/26626 A | 6/1999 |
| WO | WO 02/19991 A | 3/2002 |

OTHER PUBLICATIONS

International Search Report for PCT/FR03/02909 dated Mar. 30, 2004.
International Preliminary Examination Report for PCT/FR03/02909 dated Jan. 17, 2005.

* cited by examiner

*Primary Examiner* — Micah-Paul Young
(74) *Attorney, Agent, or Firm* — RatnerPrestia

(57) ABSTRACT

The invention relates to a directly-compressible gastro-resistant spheroid. The spheroid comprises: (i) a core containing one or more active substances; (ii) a flexible, deformable film which directly coats the aforementioned core and which comprises an enteric polymer and a mixture of saturated and/or unsaturated polyglycosylated glycerides, the fatty acids of which include at least 8 carbon atoms; and (iii) an outer water-dispersible layer containing at least one disintegrating agent. The invention further relates to multiparticular tablets comprising said spheroids.

15 Claims, No Drawings

SPHEROIDS AND MULTIPARTICULATE TABLETS COMPRISING THEM

CROSS-REFERENCE TO RELATED APPLICATIONS

This application is a division of copending U.S. application Ser. No. 10/530,052, filed Aug. 4, 2005, incorporated by reference herein in its entirety and relied upon, which is the United States national stage of International Application No. PCT/FR2003/002909, filed Oct. 3, 2003, and claiming priority under 35 U.S.C. §119 of Application Ser. No. 02/123, 33, filed in France on Oct. 4, 2002.

The present invention relates to gastroresistant spheroids coated with a flexible and deformable film, and to multiparticulate tablets comprising said spheroids.

The present invention further extends to the method of preparing such enteric spheroids and to the multiparticulate tablets comprising these spheroids.

The present invention concerns, finally, a new use of a mixture of mono-, di- and triglycerides and of polyethylene glycol monoester and diester.

By spheroids are meant spherical units whose size can vary from 0.1 mm to 2 mm, preferably from 0.1 mm to 2 mm.

The enteric coating allows the core comprising the active principle to remain intact during the residence time in the stomach, of approximately two hours, in a medium whose pH is approximately between 1 and 3. Once inside the small intestine, comprising the duodenum, jejunum and ileum, the enteric coating will dissolve rapidly in a medium whose pH is greater than 4.5 and increases steadily up to a pH of approximately 7.2 in its distal part.

The prior art includes numerous examples of multiparticulate tablets comprising coated granules.

However, it has been shown that the film formers commonly used to coat granules are unable to absorb, normally, the mechanical stresses which are applied in the course of tableting (International Journal of Pharmaceutics, No. 143, 13-23, 1996).

The tableting of coated granules is a delicate operation, altering the structure of the coating film by the appearance of fissures or by rupture; it may cause complete or partial loss of the properties of the film.

The fissuring of granules irreversibly alters the release profile of the active principle or principles they contain.

Films composed solely of enteric polymers or copolymers such as Eudragit® L30D have very mediocre mechanical properties, such that they are not resistant to tableting.

One alternative may consist of the addition to the enteric film of other polymers endowed with mechanical properties which render them suitable for tableting.

The document Drugs made in Germany 37, No. 2 (1994), p. 53 teaches that it is possible to combine Eudragit® L30D and Eudragit® NE30D to give multiparticulate tablets comprising said coated particles. Example III, however, shows that this approach does not work for all active principles.

So as to preserve the characteristics of the coating film of the granules after tableting, another solution consists in diluting the granules with auxiliary substances, whose role is to absorb the physical stresses of tableting (binders) and to allow the breakdown of the tablet (disintegrants) in a liquid medium, i.e., in aqueous solution or in the digestive fluid.

International application WO 96/01624 (Astra Zeneca) relates to a multiparticulate tablet comprising gastroresistant microgranules, wherein the proportion of said granules within the tablets is less than 75% by weight, preferably less than 60% by weight, relative to the total weight of the tablet, the remainder being a diluent which protects the granules. In the examples of the application, the proportion of enteric granules does not exceed 33% of the total weight of the tablet.

The addition of these auxiliary substances makes these forms not very suitable when the dosage is high, complicates the process by adding mixing steps, and also increases the unit cost of the formulation.

International application WO 02/19991 (Rohm) relates to a multiparticulate tablet and gastroresistant microgranules, said microgranules comprising an enteric coating of a copolymer of methacrylic acid and propylene glycol. The proportion of said granules within the tablets is between 35% and 90%, preferably 40% to 70% by weight, relative to the total weight of the tablet, the remainder being a binder.

The Applicant's International application WO 99/26608 relates to spheroids which comprise one or more active principles and are tabletable directly without the addition of a substantial part of an auxiliary substance.

These spheroids are composed of a core comprising the active principle, said core being covered with a first layer comprising at least one thermoplastic excipient whose consistency is pasty to semisolid at a temperature of the order of 20° C. and whose melting temperature is between approximately 25° C. and approximately 100° C., the resulting spheroid being itself coated with a flexible and deformable film based on a polymeric material.

Although particularly suited to the preparation of gastroresistant forms, these spheroids exhibit the disadvantage of being composed of a plurality of successive layer of different compositions, entailing a lengthy and constricting preparation process, and of using thermoplastic excipients whose pasty to semisolid consistency at 20° C. makes them not very easy to handle. There is therefore particular interest in obtaining gastroresistant spheroids devoid of any protective layer composed of thermoplastic excipients but nevertheless resistant to the stresses of tableting, such that it is possible to preserve the property of gastroresistance, and to do so without any need to add substantial amounts of auxiliaries.

The Applicant has realized that, in contrast to what is taught by the prior art, it is entirely possible to improve the mechanical properties of enteric films sufficiently to allow the production of spheroids coated with such a film, of sufficient flexibility and deformability for them to be tableted directly without the addition of more than approximately 5% by weight of auxiliary substances.

The use of Gélucire® in enteric polymer-based coatings makes it possible to improve, surprisingly, their mechanical properties in such a way that the spheroids coated with this coating composition may subsequently be tableted directly without the addition of more than approximately 5% by weight of auxiliary substances.

The present invention provides a directly tabletable gastroresistant spheroid, characterized in that it comprises:
- a core comprising one or more active principles and at least one binder, directly coated with
- a flexible and deformable film comprising an enteric polymer and a mixture of saturated and/or unsaturated polyglycosylated glycerides whose fatty acids contain at least 8 carbon atoms,
- a water-dispersible outer layer comprising at least one disintegrant.

By "directly tabletable" is meant that the spheroids can be tableted in the form of multiparticulate tablets without any need to add more than approximately 5% of auxiliary substances at the time of tableting.

The core comprises one or more active principles selected from those from the group consisting of gastrointestinal sedatives, antacids, analgesics, antiinflammatories, coronary vasodilators, peripheral and cerebral vasodilators, antiinfection agents, antibiotics, antivirals, antiparasitics, anticancer agents, anxiolytics, neuroleptics, central nervous system stimulants, antidepressants, antihistamines, antidiarrheals, laxatives, nutritional supplements, immunodepressants, hypocholesterolemics, hormones, enzymes, antispasmodics, antianginal agents, medicinal products which influence heart rate, medicinal products used in the treatment of arterial hypertension, antimigraine agents, medicinal products which influence blood clottability, antiepileptics, muscle relaxants, medicinal products used in the treatment of diabetes, medicinal products used in the treatment of thyroid dysfunctions, diuretics, anorexigenic agents, antiasthmatics, expectorants, antitussives, muco-regulators, decongestants, hypnotics, antinausea agents, hematopoietic agents, uricosuric agents, plant extracts, and contrast agents.

Particularly preferred active principles in this application are the active principles which are labile in an acid medium, necessitating gastric-acid protection for oral administration; for example, proton pump inhibitors, such as omeprazole, lansoprazole, pantoprazole, pariprazole, leminoprazole and rabeprazole, in their racemic form or in the form of pure enantiomers, themselves in base form or in the form of alkali metal salts.

Other preferred active principles are the active principles which are irritant to the mucosa of the stomach, and whose ulcerogenic effects necessitate delayed administration, such as nonsteroidal antiinflammatories, diclofenac for example, antibiotics such as erythromycin and its derivatives, and doxycycline. Finally, this form is entirely of interest for active principles which have a specific absorption site, necessitating delayed release.

The active principle or principles are applied by application to the surface of a neutral core of a mixture of sucrose and starch, or of microcrystalline cellulose, or else, according to an alternative method, are dispersed in the mass of the core, by dry, wet or hot granulation, or by extrusion with spheronization.

The active principle, initially in the form of a powder or microcrystals, is used in the form of a solution or suspension in an aqueous or organic solvent for application to neutral substances, and is used generally in the dry state in other cases.

According to the present invention the cores also comprise a binder.

The binder is selected from the group consisting in particular of cellulosic polymers, acrylic polymers, povidones, copovidones, polyvinyl alcohols, alginic acid, sodium alginate, starch, pregelatinized starch, sucroses and derivatives thereof, guar gum, polyethylene glycols, and mixtures thereof.

Among the cellulosic polymers, selection will be made advantageously of ethylcellulose, hydroxypropylcellulose, and hydroxypropylmethylcellulose, alone or in a mixture.

Among the acrylic polymers, selection is made, advantageously, of ammonio-methacrylate copolymer, the polymers and copolymers of acrylic and methacrylic acid, polyacrylates and polymethacrylates, used alone or in a mixture.

The binder is present in proportions which can range up to approximately 50% by weight, preferably up to approximately 20% by weight, relative to the weight of the uncoated cores.

Its role is to fix the active principle on the neutral substances without loss of substance, or to "glue" the powder or microcrystals of active principle and the other excipients, in order to give homogeneous particles of active principle whose size will make the coating operation easier.

The core optionally comprises a diluent and an antistat.

The diluent may be selected from the group consisting in particular of cellulosic derivatives and preferentially microcrystalline cellulose, starches on their own, lactose, polyols, preferentially mannitol, and minerals, preferentially dicalcium phosphate.

The diluent is present in proportions which can range up to approximately 95% by weight, preferably up to approximately 50% by weight, relative to the weight of the uncoated particles.

Its role is to increase the total mass of particles to be coated, and to provide a population of particles of uniform size.

The antistat may be selected from the group consisting in particular of colloidal silica, such as that sold under the brand name Aerosil®, preferably precipitated silica, such as that sold under the name Syloid® FP244, micronized or nonmicronized talc, and mixtures thereof.

The antistat is present in proportions which can range up to approximately 10% by weight, preferably up to approximately 3% by weight, relative to the weight of the uncoated particles, and enhances the fluidization of the substance when a fluidized-air bed is used, especially in the case of powder granulation.

An optional polymeric layer may be applied between the core and the flexible and deformable polymeric film, in order to isolate the active core from the polymer layer, thereby making it possible to reinforce the gastric-acid protection of the active principle.

In this case the polymer is selected from the same polymers as those used as binder. It may be identical to or different from that used as binder in the active core.

The amount of polymer applied is between 1% and 10% by weight gain relative to the mass of active cores employed, preferably between 2% and 5%.

The core comprising the active principle is subsequently coated with a flexible and deformable film which makes it possible to ensure that the active principle is protected from gastric acid, and which is composed of an enteric polymer and at least one plasticizer.

The enteric polymer is selected from the group consisting of cellulose acetate phthalate, hydroxypropylmethylcellulose phthalate, hydroxypropylmethylcellulose succinate phthalate, polyvinyl acetate phthalate, cellulose acetate trimellitate, carboxymethylcellulose, shellac or any other enteric polymer, which are used alone, in a mixture, or combined separately. The preferred polymer is the methacrylic acid copolymer sold under the brand name Eudragit® L100 or Eudragit® L30D.

The coating composition is applied by spraying to give a continuous film which covers all of the surface of each particle, irrespective of its surface condition, in an amount sufficient to ensure that the active principle is protected against gastric acid.

Protection against gastric acid is determined by means of a two-step test which consists in measuring the dissolution profile of the coated form, such that, when the latter is placed in a dissolution medium with a pH of 1.2, the percentage of active principle released after 120 minutes is less than 10% by weight, and then when, after modification of the pH of the medium from a value of 1.2 to a pH with a value of 6.8, the percentage of active principle released after 60 minutes at this pH is at least 80%, expressed by weight.

The enteric polymer is present in proportions which can range up to approximately 50%, preferably up to approximately 20%, calculated by weight gain relative to the mass of cores to be coated.

The solvent selected for spraying the enteric polymer may be water, an organic solvent, such as ethanol, isopropanol or acetone, or a mixture of solvents.

In that case the polymer is in the form of a solution, a suspension or a colloidal dispersion in the solvent or mixture of solvents. It is preferably in the form of a colloidal dispersion in water.

Optionally this polymer may be mixed with a second polymer or copolymer, which may itself be soluble or insoluble; in particular, a neutral copolymer of acrylic and methacrylic esters, sold under the brand name Eudragit® NE30D.

The addition of a second polymer to the coating composition makes it possible to enhance the mechanical properties of the enteric film resulting from this mixture. In this case the second polymer is added in an amount of not more than 100%, calculated by dry weight of polymer relative to the dry weight of the enteric polymer, preferably in a ratio of between 10% and 30%.

The mixture of saturated and/or unsaturated polyglycosylated glycerides whose fatty acids contain at least 8 carbon atoms is in particular a mixture of mono-, di- and triglycerides and of polyethylene glycol (PEG) monoester and diester, with a molecular weight of between 200 and 1500, and optionally of glycerol and of free PEG.

Said mixture is sold for example under the brand name Gélucire®.

The fatty acids of the mixture of saturated and/or unsaturated polyglycosylated glycerides preferably contain from 8 to 18 carbon atoms (C8-C18).

C8-C18 denotes mixtures, in significant and variable proportions, of caprylic (C8), capric (C10), lauric (C12), myristic (C14), palmitic (C16), and stearic (C18) acid, when these acids are saturated, and the corresponding unsaturated acids (C8-C18). The proportions of these fatty acids may vary depending on the starting-product oils.

Among the Gélucires®, preference is given to Gélucire® 50/13, which thus comprises predominantly palmitostearic acid (C16-C18) and is characterized by a melting point of between 46.0 and 51.0° C. and a hydrophilic/lipophilic balance (HLB) of 13.

The total proportion of the mixture of saturated and/or unsaturated polyglycosylated glycerides is not more than 40%, preferably between 10% to 30%, expressed by weight relative to the dry weight of polymer.

The function of the mixture of saturated and/or unsaturated polyglycosylated glycerides is to lower the glass transition temperature of the film and to enhance the mechanical properties of the polymeric coating film; in particular, to render it flexible and deformable.

Optionally the coating film further comprises a plasticizer selected from the group consisting of triethyl citrate, acetyl tributyl citrate, triacetin, tributyl citrate, diethyl phthalate, polyethylene glycols, polysorbates, and mono- and diacetylated glycerides.

The plasticizer is used in a total proportion of not more than 40%, preferably between 10% to 30%, expressed by weight relative to the dry weight of polymer.

The function of the plasticizer is to lower the glass transition temperature of the film.

The coating composition optionally further comprises a surfactant, an antistat and/or a lubricant.

The surfactant is selected from anionic, cationic, nonionic or amphoteric surfactants.

The antistat is used in order to avoid the problems associated with static electricity. It is in the group consisting of micronized or nonmicronized talc, colloidal silica (Aerosil® 200), treated silica (Aerosil® R972), or precipitated silica (Syloid® FP244), and mixtures thereof.

The antistat is used in a proportion of not more than approximately 10% by weight, preferably between 0 and 3%, and preferably less than approximately 1% by weight.

The lubricant is selected from the group consisting of magnesium stearate, stearic acid, sodium stearyl fumarate, micronized polyoxyethylene glycols, sodium benzoate, and mixtures thereof.

The particle size of these spheroids allows them to be used in the production of multiparticulate tablets.

Advantageously the spheroids have a diameter of between 0.1 mm and 2 mm, preferably between 0.3 mm and 1 mm.

The size is determined by conventional techniques; for example, with the aid of a set of calibrated-mesh screens, or by laser diffraction.

The spheroids according to the invention are advantageously coated with a water-dispersible outer layer.

This layer ensures the mutual cohesion of the spheroids at the time of tableting and thus ensures the hardness of the tablet, and allows disintegration of the resulting tablet in aqueous medium.

The water-dispersible outer layer is composed of at least one disintegrant.

The disintegrant is selected from the group consisting in particular of the crosslinked sodium carboxymethylcellulose denoted in the art by the term croscarmellose, crospovidone, sodium carboxymethyl starch, and mixtures thereof.

It may optionally comprise a binder selected from those used for the assembly step, and water-soluble auxiliary substances such as polyols, in particular mannitol.

The invention likewise relates to the method of preparing the directly tabletable gastroresistant spheroids.

The method in accordance with the invention comprises the following steps:
  preparing a core comprising one or more active principles and at least one binder;
  coating the cores thus obtained by spraying the coating composition comprising an enteric polymer and a mixture of saturated and/or unsaturated polyglycosylated glycerides whose fatty acids contain at least 8 carbon atoms, preferably from 8 to 18 carbon atoms (C8-C18);
  coating the gastroresistant spheroids with a water-dispersible outer layer comprising at least one disintegrant; and
  drying the spheroids.

According to this embodiment the steps may be carried out within different apparatus or the same apparatus.

The core comprising the active principle may be obtained by granulation, by application to neutral substance, or else by extrusion with spheronization.

In a first embodiment the cores comprising the active principle are prepared by granulation according to the following steps:
  dry-mixing the active principle in the form of powder or microcrystals, optionally with the diluent and an antistat;
  granulating the mixture obtained by spraying a solution of the binder;
  drying.

For granulation, a high-energy granulator, a planetary mixer or a fluidized-air bed are advantageously used.

In a second embodiment of the cores comprising the active principle, said cores are prepared by application to neutral substances according to the following steps:

spraying onto neutral substances a solution or suspension of the active principle, comprising the dissolved binder and, optionally, a lubricant, an antistat;

drying.

The application preparation may, depending on the case in hand, be in the form of a suspension in aqueous or organic media, in the form of solutions, in the form of emulsions, or in the melted state.

In a first variant of the application method, the active principle is incorporated into the application preparation.

According to another variant of the application method, the active principle is applied by dusting to the neutral cores wetted beforehand with the application preparation.

All of the steps of the method according to the invention may be carried out in a pan-coating turbine, in a perforated turbine or in a fluidized-air bed.

According to a third embodiment, the cores comprising the active principle are prepared by extrusion with spheronization.

In that case the active principle is mixed into the mass of excipient. The mixture is wetted in order to ensure satisfactory extrusion, and the extrudates thus obtained are calibrated and spheronized.

The cores thus obtained are subsequently coated by means of a composition comprising a film-forming enteric polymer, a plasticizer, and, optionally, a surfactant, an antistat and/or a lubricant.

The coating composition is sprayed in the form of a solution, a suspension or a colloidal dispersion of this polymer in an aqueous or organic solvent, and then dried.

The water-dispersible outer layer is applied with one of the above techniques, but isopropyl alcohol is the solvent preferably used.

In one preferred embodiment of the method of preparing gastroresistant spheroids, all of the steps of preparing the active core and coating are carried out in a fluidized-air bed.

The fluidized-air bed is equipped with a spraying nozzle whose position and spraying orientation are selectable. The spraying mode is referred to as "top spray", "bottom spray" or "tangential spray", in accordance with the customary terminology of the skilled worker.

The selection of the spraying mode makes it possible to master the growth kinetics of the particles and to prevent sticking phenomena, associated with the nature of the active principle, with the binder or coating composition sprayed, and with the various parameters of the method (temperature, air pressure, for example, flow rate of solution).

The present invention likewise provides multiparticulate tablets comprising the aforedescribed directly tabletable spheroids and comprising not more than approximately 5% by weight in total of an auxiliary substance, such as a lubricant, an antistat and/or a permeabilizing agent.

The lubricant is selected from the group consisting of magnesium stearate, stearic acid, sodium stearyl fumarate, micronized polyoxyethylene glycols, sodium benzoate, and mixtures thereof.

The antistat is used in order to avoid problems associated with static electricity. It is in the group consisting of micronized or nonmicronized talc, colloidal silica (Aerosil® 200), treated silica (Aerosil® R972) or precipitated silica (Syloid® FP244), and mixtures thereof.

The permeabilizing agent is selected from the group consisting in particular of silicas having high affinity for aqueous solvents, such as the precipitated silica better known under the brand name Syloid®, maltodextrins, β-cyclodextrins, and mixtures thereof.

The permeabilizing agent makes it possible to create a hydrophilic network which hence contributes to more effective breakdown of the tablet.

The multiparticulate tablets according to the invention disintegrate in solution in less than 60 minutes and restore independent spheroids, such that the release profile of the tablet and of the spheroids constituting it are virtually equivalent.

This is because the tablets according to the invention allow the delivery of spheroids without the release profile of the active principle or principles they contain being adversely affected under the effect of tableting.

The tablets according to the invention may be composed solely of spheroids according to the invention or of a mixture of spheroids comprising one or more active principles and of placebo spheroids: that is, spheroids in accordance with the present invention but without active principle.

The tablets according to the invention may be subjected to a final coating for protection or coloration.

The invention likewise relates to the method of preparing multiparticulate tablets comprising the spheroids.

The method according to the invention comprises the following steps:

mixing the gastroresistant spheroids with not more than 5% by weight in total of one or more auxiliary substances, such as a lubricant, an antistat and/or a permeabilizing agent;

tableting the mixture to give a unitary form.

The spheroids can be tableted on an alternating or rotary tableting machine.

The stresses exerted on the spheroids during the tableting step may vary from 5 kN to 50 kN and preferably between 5 kN and 15 kN.

The hardness of these tablets is preferably between 1 and 10 kp, more preferably between 1 and 5 kp, measured in accordance with the method of the European Pharmacopeia (2.9.8), 1 kp being equal to 9.8N.

The hardness of the multiparticulate tablet is preferably adapted so as to give a friability, measured according to the method of the European Pharmacopeia, of less than 2%.

The breakdown time of the tablets in an aqueous medium at 37° C. is less than 60 minutes.

The tablets may have a diameter of between 6 mm and 17 mm. Their shape may be round, oval, oblong, with a flat or concave surface, and may have grooves or bars for divisibility.

The tablets according to the invention preferably have a mass of between 0.1 g and 2 g.

The invention will be better understood by means of the examples of preparation of gastroresistant spheroids and of multiparticulate tablets according to the invention.

These examples are given solely by way of illustration and of advantageous embodiments of the invention, and in no way constitute any limitation thereon.

Analytical Techniques [USP-724]

Gastroresistance Test

The dissolution profile of the gastroresistant spheroids is determined under the following conditions:

Apparatus: USP type II
Blade speed: 100 rpm
Volume: 750 ml pH 1.2 and 1000 ml pH 6.8
Temperature: 37.0° C.±0.5° C.

Detection: direct UV spectrophotometry at 272 nm
Dissolution medium: 0.1N HCl (pH=1.2) for 120 minutes (t0 to t 120 min), then pH 6.8 for 60 min (t=121 min to t=180 min)

EXAMPLE 1

Application of the Active Principle in Fluidized-Air Bed

In a fluidized-air bed of type GPCG-3, equipped with a Würster ("bottom spray") nozzle, 318.5 grams of neutral cores are sprayed with a suspension containing 636.9 grams of theophylline and PEG400 as binder, 30% by weight relative to the theophylline.

Coating 1000 grams of granules obtained after the application step described above are coated in a Glatt GPCG-3 fluidized-air bed equipped with a Würster insert by spraying with an aqueous dispersion of Eudragit® L30D containing 30% by weight of triethyl citrate (TEC), calculated relative to the dry weight of polymer.

A total quantity of Eudragit® L30D corresponding to 30%, calculated as weight gain relative to the initial mass of uncoated granules, is applied to the theophylline granules.

The coated granules G1 obtained from the coating step have the following dissolution profile:

TABLE 1

| Theophylline released % (w/w) | |
|---|---|
| Time | G1 |
| pH 1.2 | |
| 120 min → pH 6.8 | 7 |
| 135 min | 81 |
| 150 min | 81 |
| 180 min | 81 |

Conclusion

The spheroids have a dissolution profile which meets the specifications of the gastroresistance test.

EXAMPLE 2

Overcoating

The granules G1 from example 1 are coated with an outer layer composed of a binder but devoid of disintegrant.

The granules G1 are sprayed with an aqueous solution containing either PEG 4000 or a mixture of PEG 4000 and HPMC 603 in a 20/80 ratio, additionally comprising 20% by weight of micronized talc, calculated relative to the total dry weight of polymer.

Each sub-batch of granules is tableted separately on a Manesty F3 press equipped with a circular, convex punch with a diameter of 10 mm, so as to give a friability value of less than 2% by weight.

After 60 minutes, the tablets thus obtained have not disintegrated.

Conclusion:

The dispersible outer layer devoid of a disintegrant does not allow the tablet to break down in accordance with the specifications.

EXAMPLE 3

Overcoating

The granules G1 from example 1 are coated with a water-dispersible layer comprising a disintegrant, Ac-Di-Sol®.

The Ac-Di-Sol®, mixed with mannitol 25 in a 50/50 ratio, is applied to the granules G1 by dusting in a conventional turbine, using a binder solution comprising polyvinylpyrrolidone (PVP) K29, in 10% solution in isopropyl alcohol.

A quantity of Ac-Di-Sol® corresponding to 20% by weight, calculated relative to the initial mass of granules G1, is applied to the granules.

The granules G1/1 thus prepared have the following dissolution profile:

TABLE 2

| Theophylline released % (w/w) | |
|---|---|
| Time | G1/1 |
| pH 1.2 | |
| 120 min → pH 6.8 | 7 |
| 135 min | 79 |
| 150 min | 79 |
| 180 min | 80 |

Tableting

The granules obtained in the preceding step, G1/1, are tableted on a Manesty F3 press equipped with a circular, convex punch with a diameter of 10 mm, to give a unit dose of theophylline of approximately 50 mg.

The tablets (C1/1) thus obtained have the following characteristics:

TABLE 3

| | C1/1 |
|---|---|
| Weight (mg) | 426 |
| Hardness (kP) | 2.7 |
| Friability (%) | 0.21 |
| Break down (min) | 50 |
| Theophylline released % (w/w) | |
| pH 1.2 | |
| 120 min → pH 6.8 | 51 |
| 135 min | 87 |
| 150 min | 88 |
| 180 min | 88 |

Conclusion:

The water-dispersible layer comprising Ac-Di-Sol® allows the tablet to break down in less than 60 minutes, but the tableting of the granules causes the polymeric film to rupture and the gastric-acid protection to be lost.

The tablet does not meet the specifications of the gastroresistance test.

EXAMPLE 4

Overcoating

The granules G1 from example 1 are coated with a water-dispersible layer comprising a disintegrant, Kollidon® CLM.

The Kollidon® CLM, mixed with mannitol 25 in a 50/50 ratio, is applied to the granules G1 by dusting in a conventional turbine, using a binder solution comprising PVP K29, in 10% solution in isopropyl alcohol.

A quantity of Kollidon® CLM corresponding to 20% by weight, calculated relative to the initial mass of granules G1, is applied to the granules.

The granules thus prepared (G1/2) have the following dissolution profile:

TABLE 4

| Theophylline released % (w/w) | |
|---|---|
| Time | G1/2 |
| pH 1.2 | |
| 120 min | 5 |
| → pH 6.8 | |
| 135 min | 82 |
| 150 min | 82 |
| 180 min | 82 |

Tableting

The granules obtained in the preceding step are tableted on a Manesty F3 press equipped with a circular, convex punch with a diameter of 10 mm, to give a unit dose of theophylline of approximately 70 mg.

The tablets (C1/2) thus obtained have the following characteristics:

TABLE 5

| | C1/2 |
|---|---|
| Weight (mg) | 409 |
| Hardness (kP) | 2.5 |
| Friability (%) | 0.51 |
| Break down (min) | 32 |
| Theophylline released % (w/w) | |
| pH 1.2 | |
| 120 min | 41 |
| → pH 6.8 | |
| 135 min | 80 |
| 150 min | 81 |
| 180 min | 82 |

Conclusion:

The water-dispersible layer comprising the disintegrant allows the tablet to break down in less than 60 minutes, but the tableting of the granules causes the polymeric film to rupture and the gastric-acid protection to be lost.

The tablet does not meet the specifications of the gastroresistance test.

EXAMPLE 5

Application of the Active Principle in Fluidized-Air Bed (RD239)

In a fluidized-air bed of type Glatt GPCG-3, equipped with a Würster nozzle, 318.5 grams of neutral cores are sprayed with a suspension containing 636.9 grams of theophylline and a PVPK29/Eudragit® RS100 mixture as binders, representing in total 50% by weight relative to the theophylline.

Coating 1000 grams of granules obtained after the application step are coated in a Glatt GPCG-3 fluidized-air bed equipped with a Würster insert by spraying with an aqueous dispersion of a Eudragit® L30D/Gélucire® 50/13 mixture in a 75/25 ratio, additionally comprising 10% by weight of triethyl citrate (TEC), calculated relative to the dry weight of Eudragit® L30D.

A total quantity of the Eudragit® L30D/Gélucire® 50/13 mixture corresponding to 50%, calculated as weight gain relative to the initial mass of uncoated granules, is applied to the granules.

The coated granules G2 thus coated have the following dissolution profile:

TABLE 6

| Theophylline released % (w/w) | |
|---|---|
| Time | G2 |
| pH 1.2 | |
| 120 min | 3 |
| → pH 6.8 | |
| 135 min | 92 |
| 150 min | 109 |
| 180 min | 110 |

Overcoating

The granules G2 obtained in the preceding step are coated with a water-dispersible layer comprising Kollidon® CLM.

The Kollidon® CLM, mixed with mannitol 25 in a 50/50 ratio, is applied to the granules by dusting in a conventional turbine, using a binder solution comprising PVP K29, in 10% solution in isopropyl alcohol.

A quantity of Kollidon® CLM corresponding to 20% by weight, calculated relative to the initial mass of granules G2, is applied to the granules.

Tableting

The coated granules obtained in the preceding step (G2/1) are tableted on a Manesty F3 press equipped with a circular, convex punch with a diameter of 12 mm, to give a unit dose of theophylline of approximately 150 mg.

The tablets (C2/1) thus obtained have the following characteristics:

TABLE 7

| | C2/1 |
|---|---|
| Weight (mg) | 400 |
| Hardness (kP) | 6.0 |
| Friability (%) | Nd |
| Break down (min) | 26 |
| Theophylline released % (w/w) | |

TABLE 7-continued

| | C2/1 |
|---|---|
| pH 1.2 | |
| 120 min → pH 6.8 | 3 |
| 135 min | 64 |
| 150 min | 89 |
| 180 min | 92 |

Conclusion

The spheroids meet the specifications of the gastroresistance test.

The tablet meets the specifications of the disintegration and gastroresistance test.

What is claimed is:

1. An oral multiparticulate tablet comprising gastroresistant spheroids, wherein each spheroid comprises:
   (i) a core comprising one or more active principles, directly coated with
   (ii) a flexible and deformable film comprising an enteric polymer and a mixture of saturated and/or unsaturated polyglycosylated glycerides whose fatty acids contain at least 8 carbon atoms, and
   (iii) a water-dispersible outer layer comprising at least one disintegrant, and wherein said oral multiparticulate tablet contains not more than approximately 5% by total weight of one or
   more auxiliary substances added at the time of tableting, wherein the tablet has a hardness ranging from 1 kp to 10 kp, wherein the auxiliary substance is a lubricant, an antistat and/or a permeabilizing agent, wherein the enteric polymer is a methacrylic acid copolymer and the mixture of saturated and/or unsaturated polyglycosylated glycerides is a mixture of mono-, di- and triglycerides whose fatty acids contain from 8 to 18 carbon atoms (C8-C18) and of polyethylene glycol monoester and diester, with a molecular weight of between 200 and 1500, and of glycerol and/or of free PEG, and wherein the disintegrant is selected from the group consisting of the crosslinked sodium carboxymethylcellulose denoted in the art by the term croscarmellose, crospovidone, sodium carboxymethyl starch, and mixtures thereof, said oral multiparticulate tablet is configured to disintegrate in solution in less than 60 minutes and is configured to restore independent spheroids, such that the release profile of the tablet and of the spheroids constituting it are equivalent.

2. The multiparticulate tablet of claim 1, which comprises a mixture of said spheroids comprising one or more active principles with placebo spheroids.

3. The multiparticulate tablet of claim 1, wherein the core of the spheroids comprises one or more active principles selected from the group consisting of gastro-intestinal sedatives, antacids, analgesics, anti-inflammatories, coronary vasodilators, peripheral and cerebral vasodilators, antiinfection agents, antibiotics, antivirals, antiparasitics, anticancer agents, anxiolytics, neuroleptics, central nervous system stimulants, antidepressants, antihistamines, anti-diarrheals, laxatives, nutritional supplements, immuno-depressants, hypocholesterolemics, hormones, enzymes, antispasmodics, antianginal agents, medicinal products which influence heart rate, medicinal products for treating arterial hypertension, antimigraine agents, medicinal products which influence blood clottability, antiepileptics, muscle relaxants, medicinal products for treating diabetes, medicinal products for treating thyroid dysfunctions, diuretics, anorexigenic agents, antiasthmatics, expectorants, antitussives, muco-regulators, decongestants, hypnotics, antinausea agents, hematopoietic agents, uricosuric agents, plant extracts, and contrast agents.

4. The multiparticulate tablet of claim 1, wherein the active principle is selected from the group consisting of proton pump inhibitors, in their racemic form or in the form of pure enantiomers, themselves in base form or in the form of alkali metal salts; nonsteroidal anti-inflammatories, in the form of bases or of salts; and antibiotics, in the form of bases or of salts.

5. The multiparticulate tablet of claim 4, wherein the proton pump inhibitors are selected from the group consisting of omeprazole, lansoprazole, pantoprazole, pariprazole, leminoprazole and rabeprazole.

6. The multiparticulate tablet of claim 4, wherein the nonsteroidal anti-inflammatory is diclofenac.

7. The multiparticulate tablet of claim 4, wherein the antibiotics are selected from the group consisting of erythromycin and its derivatives.

8. The multiparticulate tablet of claim 1, wherein the core of the spheroids further comprises a binder selected from the group consisting of cellulosic polymers, acrylic polymers, povidones, copovidones, polyvinyl alcohols, alginic acid, sodium alginate, starch, pregelatinized starch, sucroses and derivatives thereof, guar gum, polyethylene glycols, and mixtures thereof.

9. The multiparticulate tablet of claim 1, wherein said mixture predominantly comprises palmitostearic acid and has a melting point of between 46.0° C. and 51.0° C. and a hydrophilic/lipophilic balance (HLB) of 13.

10. The multiparticulate tablet of claim 1, wherein the flexible and deformable film comprises a plasticizer selected from the group consisting of triethyl citrate, acetyl tributyl citrate, triacetin, tributyl citrate, diethyl phthalate, polyethylene glycols, polysorbates, and monoacetylated and diacetylated glycerides.

11. The multiparticulate tablet of claim 10, wherein the plasticizer is triethyl citrate.

12. The multiparticulate tablet of claim 1, wherein the flexible and deformable film further comprises a surfactant, an antistat and/or a lubricant.

13. The multiparticulate tablet of claim 1, wherein the water dispersible outer layer further comprises a binder and an auxiliary substance.

14. The multiparticulate tablet of claim 13, wherein the auxiliary substance is mannitol.

15. A method of preparing multiparticulate tablets of claim 1 comprising the following steps:
   (i) mixing the gastroresistant spheroids with not more than approximately 5% by weight in total of one or more auxiliary substances, and
   (ii) tableting the mixture to give a unitary form, wherein a stress of 5 kN to 50 kN is exerted on the mixture during the tableting step.

* * * * *